US00PP09840P

United States Patent [19]

Lamb

[11] Patent Number: Plant 9,840

[45] Date of Patent: Mar. 25, 1997

[54] CALATHEA PLANT NAMED 'SATURN'

[75] Inventor: Ann E. Lamb, Sebring, Fla.

[73] Assignee: Twyford International, Inc., Santa Paula, Calif.

[21] Appl. No.: 548,870

[22] Filed: Oct. 26, 1995

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—Foley & Lardner

[57] ABSTRACT

A Calathea plant named 'Saturn' having leaves centrally marked with silver-green with a dark green margin, with other horticultural properties being similar to *Calathea picta royal* from which it is derived.

1 Drawing Sheet

The present invention comprises a new and distinct cultivar of Calathea, botanically known as *Calathea picta royal,* and referred to by the cultivar name 'Saturn'.

The new cultivar was discovered and selected by the inventor Ann E. Lamb from tissue culture-derived plants of *C. picta royal* in Apopka, Fla., in December 1993. Propagation by division done under the supervision of the inventor in Apopka, Fla. was used to increase the number of plants for evaluation and has demonstrated the stability of the combination of characteristics from generation to generation.

The following traits have been repeatedly observed to be characteristics which in combination distinguish 'Saturn' from other plants of the type *C. picta royal,* and from the patented cultivar *C. roseo picta* 'Rosy' disclosed in U.S. Pat. No. 8,836.

1. Plants of 'Saturn' produce leaves having silver-green centers which are bordered with dark green. Unlike 'Rosy', leaf blades of 'Saturn' have no pink markings.

2. The leaf midrib of 'Saturn' is often tinged with pink, particularly when juvenile.

3. The growth rate and habit of 'Saturn' is similar to *Calathea picta royal* and differs from 'Rosy' in the following ways:

a) It is taller and more upright.
b) The leaves are larger and more oblong.
c) It produces fewer branches.
d) It is more tolerant of adverse growing conditions.
e) It is suitable for larger pot sizes.
f) It is faster growing.

The following observations, measurements and values describe plants grown in Apopka, Fla. under greenhouse conditions which closely approximate those generally used in horticultural practice.

All color references are measured against The Royal Horticulural Society color chart. Colors are approximate as color depends on horticultural practices such as light level and fertilization rate, among others, without, however any variance in genotype.

The color photographic drawing comprises a top perspective view of a plant of 'Saturn' in a 15.5 cm pot approximately 30 weeks after planting a 16-week-old liner obtained by tissue culture and grown under appropriate growing conditions. Colors are as accurate as possible with color illustrations of this type.

Origin: Mutation of *Calathea picta royal.*
Classification: *Calathea picta royal,* cv, 'Saturn'.
Propagation: Asexual propagation either by tissue culture or division.

Plant: In a 15.5 cm pot for a plant grown from a 30-week-old liner after 16 weeks under appropriate growing conditions, 'Saturn' is approximately 18 cm to 25 cm in height and approximately 37 cm to 42 cm in width.

Leaves:

*Form.*—The leaf blade is oblong to orbicular with a mucronate tip and an obtuse base. The margins are entire. The midrib tends to be straight, or curved upward slightly over the length of the leaf. The leaf blade is wavy over the width of the leaf.

*Size.*—Leaf blades are approximately 14.3 cm to 17.5 cm in length and approximately 12 cm to 13.7 cm in width.

*Petiole.*—The petiole is approximately 10.9 cm to 13.3 cm in height from the base of the petiole to the base of the leaf blade on the primary shoot. Secondary shoots are somewhat smaller depending on the age of the shoot. The petiole is approximately 4 mm in diameter just below the geniculum. The petiole below the geniculum is straight.

*Petiole wings.*—Petiole wings are approximately 7.8 cm in length and approximately 8 mm in width at their midpoint. The tip of the petiole wing is rounded. There is approximately 6 mm to 12 mm between the top of the wing and the base of the geniculum.

*Geniculum.*—The geniculum is approximately 19 mm in length, and approximately 5 mm in diameter. The color is greener than but closest to 166 A. There is no space between the top of the geniculum and the base of the leaf blade. The geniculum is prominent. The orientation of the leaf to the petiole is variable, as the geniculum bends. During the night and early morning, the geniculum is straight, and the leaf is held nearly vertical above the petiole. During the day, the geniculum is bent, and the leaf is oriented approximately 90 degrees to the petiole.

*Veins.*—Veins and midrib are sunken, with the leaf blade slightly concave between veins on the upper surface. The midrib protrudes from the lower surface. Primary veins on leaves radiate out from the midrib along the length of the leaf. Veins are recessed within the leaf. There are approximately 12–14 primary veins one the leaf. The veins are darker in color than the tissue surrounding them (147 B).

*Color/Pattern.*—The upper surface of the leaf blade is silver-green in the center, with a dark green margin. The silver-green central area has a thin dark green border. The leaf midrib is silver-green, often tingled with pink. Upper surface: Margin: Much darker than, but closest to 147 A, with a thin border which is much darker than, but closest to 139 A. Leaf center: Predominantly 147 C, darker areas of 147 B line the midrib. Midrib: 147 B, 184 A when juvenile. Lower surface: Entirely 187 A. Midrib: Greener than, but closest to 177 A. Petiole: 187 A. Petiole wing: Lighter than, but closest to 187 A.

Inflorescence: The inflorescence of 'Saturn' is typical of the species *Calathea picta royal* and has no commercial significance.

Roots: Dark brown fibrous roots with fine laterals.

It is claimed:

1. A new and distinct cultivar of Calathea plant named 'Saturn', as illustrated and described.

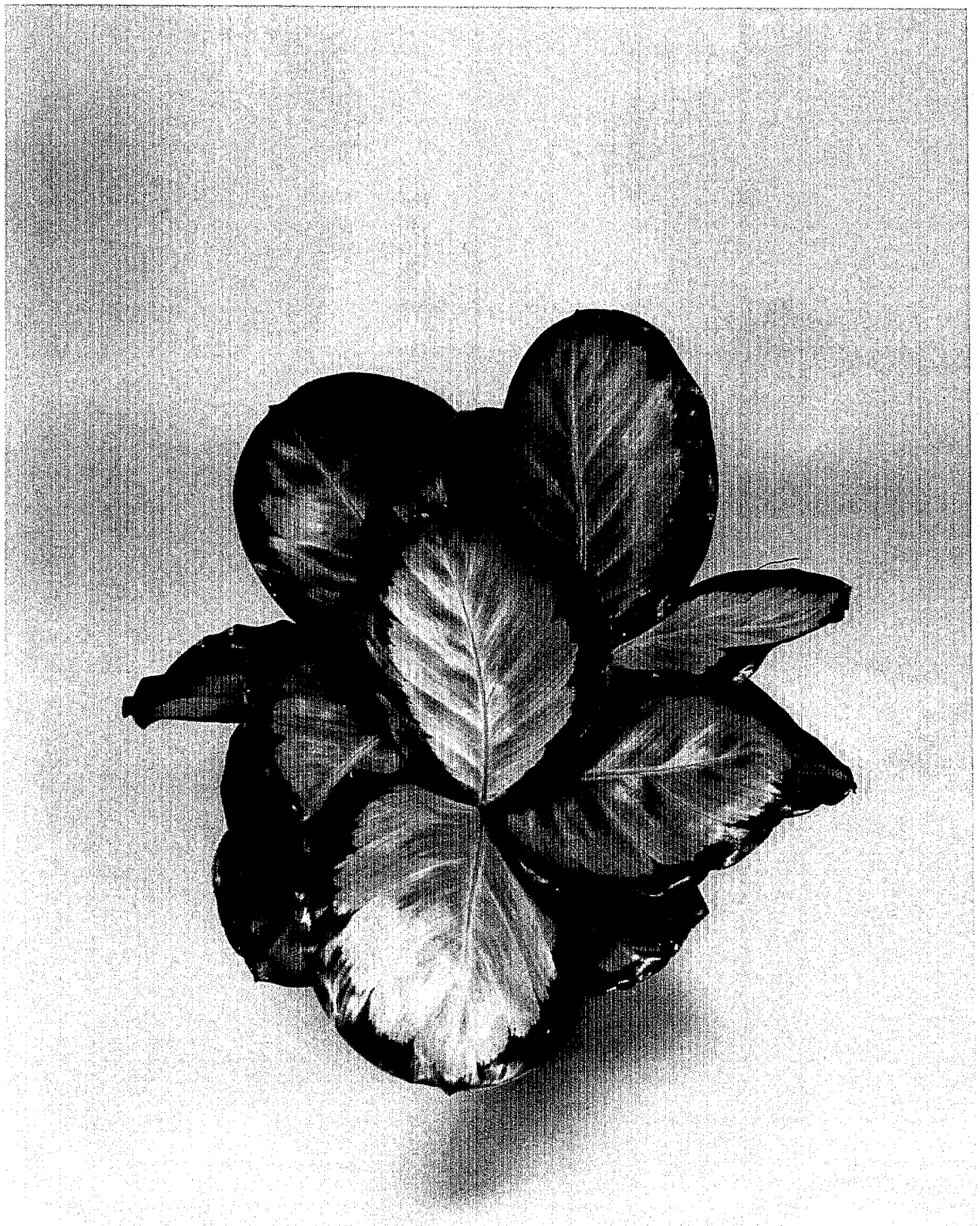

* * * * *